United States Patent [19]

Kanazawa

[11] Patent Number: 5,330,782
[45] Date of Patent: Jul. 19, 1994

[54] METHOD FOR PREPARATION OF COLORED POROUS POLYTETRAFLUOROETHYLENE MATERIAL

[75] Inventor: Shin-ichi Kanazawa, Osaka, Japan

[73] Assignee: Sumitomo Electric Industries, Ltd., Osaka, Japan

[21] Appl. No.: 955,876

[22] PCT Filed: Apr. 10, 1992

[86] PCT No.: PCT/JP92/00456
§ 371 Date: Dec. 11, 1992
§ 102(e) Date: Dec. 11, 1992

[87] PCT Pub. No.: WO92/18563
PCT Pub. Date: Oct. 29, 1992

[30] Foreign Application Priority Data
Apr. 11, 1991 [JP] Japan .................................. 3-106686

[51] Int. Cl.⁵ .............................................. A01N 1/02
[52] U.S. Cl. ...................................... 427/2.25; 8/506; 427/316; 623/1

[58] Field of Search ................ 427/2, 244, 393.5, 316; 8/506; 623/1

[56] References Cited

U.S. PATENT DOCUMENTS 5,064,593 11/1991 Tamara et al. ...................... 264/113
5,104,400 4/1992 Berguer et al. ................. 264/127 X

FOREIGN PATENT DOCUMENTS 116465 11/1975 Fed. Rep. of Germany .
54-139972 10/1979 Japan .
62-91549 4/1987 Japan .
3-199475 8/1991 Japan .

Primary Examiner—Michael Lusignan
Attorney, Agent, or Firm—Cushman, Darby & Cushman

[57] ABSTRACT

A colored porous polytetrafluoroethylene material prepared by impregnating a colorant in a porous polytetrafluoroethylene material having a fine fiber structure consisting of fibers and nodes connected to one another through the fibers, and then heating the porous material at a temperature of at least a melting point of the porous material has porosity inherently possessed by the porous material and no distortion of a colored line.

15 Claims, 3 Drawing Sheets

METHOD FOR PREPARATION OF COLORED POROUS POLYTETRAFLUOROETHYLENE MATERIAL

FIELD OF THE INVENTION

The present invention relates to a method for preparing a colored porous polytetrafluoroethylene material. The present invention can be applied in various fields, for example, an artificial blood vessel having a reference line formed by the coloring.

RELATED ART

A porous material made of polytetrafluoroethylene (abbreviated as "PTFE") has excellent properties possessed by PTFE, such as thermal resistance, chemical resistance, electrically insulating properties, non-tackiness, flame retardant properties, lubricating ability and the like and it is utilized in various fields. In particular, a porous PTFE material prepared by an expanding method has a fine fibrous structure consisting of very fine fibers and nodes connecting to one another through the fibers, and a pore size and a porosity thereof can be freely changed. Accordingly the porous PTFE material is utilized in an extensive range of applications, for example, a filter material such as a membrane filter, a permeable membrane, an electrically insulative material, a material for an artificial organ such as an artificial blood vessel and an artificial lung, and an endoscope tube.

Depending on the application of the porous PTFE material, for example, the presence of a colored line representing a straight line or lattice is required so that the presence of the sag or torsion is evaluated or a size is indicated.

Hitherto, the following methods for the coloring were known: (1) a method comprising coating a paint such as an ink on a porous material prepared by the expansion and calcination, to physically adhere a colorant to a porous material surface, (2) a method comprising mixing a PTFE resin with a colorant during the preformation of the PTFE resin, and then expanding and calcining the mixture to support the colorant by the thermal fusion, and (3) a method comprising coating a colorant on a porous material prepared by the expansion and calcination, and then wrapping a PTFE tape around the porous material to support the colorant.

The physical adhesion method (1) is an easy method for the coloring. However, it gives a large amount of a deposits, and accordingly is unsuitable for a filter material, an artificial organ and a medical material. The paint is generally prepared by dissolving or dispersing a pigment in a solvent. Since the paint is coated on the porous PTFE material surface and the pigment is merely physically adhered or absorbed to the surface, the pigment is necessarily deposited when the paint contacts with a liquid. The thermal fusion method (2) has the defects that the procedure for preparing the porous material is complex, the distortion of the colored line cannot be prevented during the preparation, and the deposition of the colorant cannot be sufficiently suppressed only by the thermal fusion on the resin. In the method (3), since the PTFE tape is wrapped around the coated surface, the deposition can be prevented to some extent, but porosity inherently possessed by the porous PTFE material is easily damaged and the preparation procedure is complex.

SUMMARY OF THE INVENTION

One object of the present invention is to provide a method for preparing a colored porous PTFE material in which the deposition of a colorant is suppressed without damaging the porosity.

Another object of the present invention is to provide a method for preparing a colored porous PTFE material in which a colored line can be easily provided on a porous PTFE material to evaluate the shape (e.g. linearity and distortion) thereof and indicate the size, and the colored line is not distorted during the preparation procedure.

Accordingly, the present invention provides a method for preparing a colored porous polytetrafluoroethylene material which comprises impregnating a colorant in a porous polytetrafluoroethylene material having a structure consisting of fibers and nodes connected to one another through the fibers, and then heating a portion impregnated with the colorant at a temperature of at least a melting point of the porous material.

According to the present invention, the porosity inherently possessed by the porous PTFE material is not damaged, the colored line is not distorted during the preparation procedure, and the preparation steps are relatively easy.

DETAILED DESCRIPTION OF THE INVENTION

Hereinafter, the present invention is described in detail by reference to the attached drawings.

Figure 1:
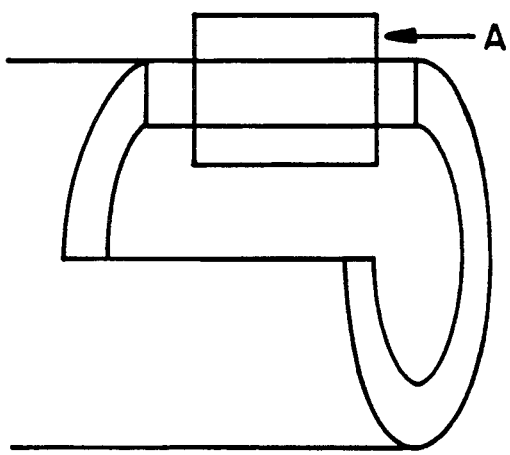
FIG. 1 shows schematic views of a porous PTFE tube and a cross-section thereof.
Figure 2:
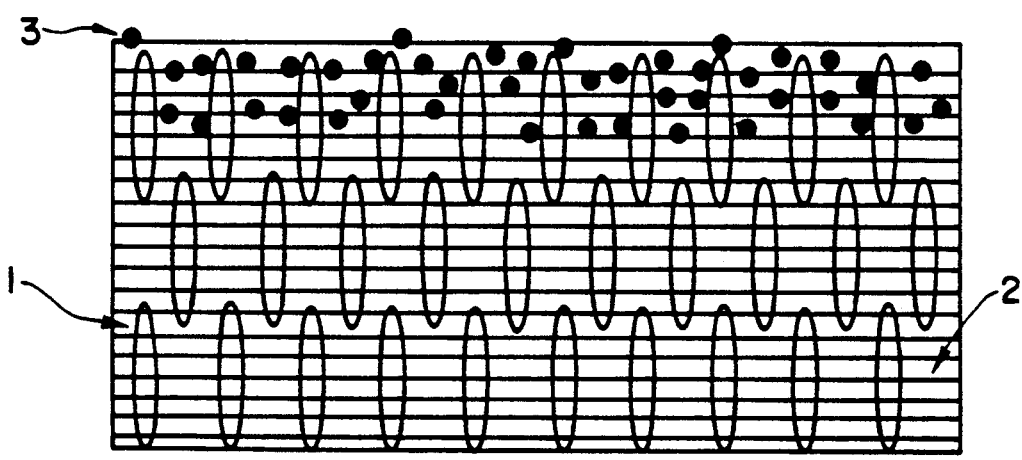
FIG. 2 is an enlarged schematic view of the cross-section A in FIG. 1 and shows a fine fiber structure and a state that a porous material is impregnated with a colorant.

FIGS. 1 to 4 are conceptional drawings for the method of the present invention. FIG. 1 shows a porous PTFE material prepared by the expansion or stretching and calcination, for example, sintering, and FIG. 2 shows an enlarged view of a cross-section A of FIG. 1. As shown in FIG. 2, the porous PTFE material has a fine fiber structure consisting of fibers 2 and nodes 1 connected to one another through the fibers 2. When a surface of the porous material is coated with a paint in which a colorant is dissolved or dispersed in an organic solvent, the colorant 3 is incorporated in a pore between the nodes.

Figure 3:
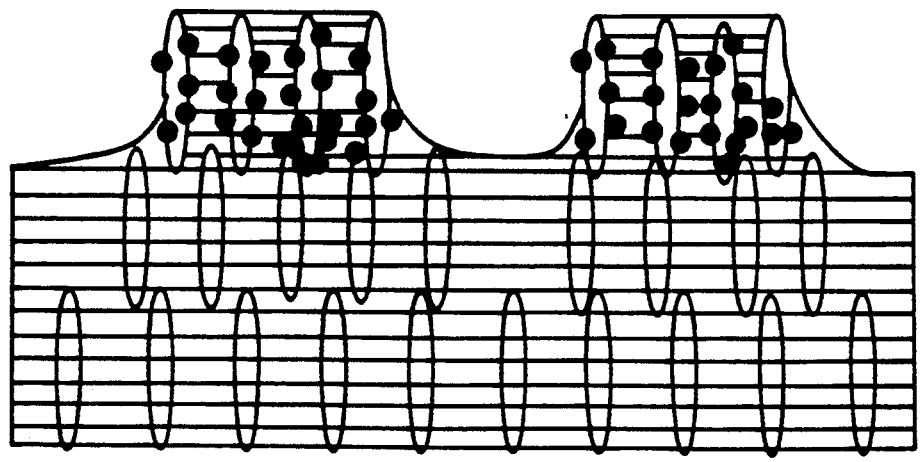
FIG. 3 is a schematic view showing that the heating causes a shrinkage of a portion impregnated with the colorant between nodes.

Then, when the surface coated with the colorant is heated at at least a melting point of PTFE, a portion impregnated with the colorant between the nodes shrinks as shown in FIG. 3. Namely, the heating cuts some of fibers between the nodes so that a distance between the nodes between which the fiber cuts is lengthened and a distance between the nodes between which the fiber does not cut is shortened. Simultaneously, the fusion of the colorant to the PTFE resin proceeds. Finally, a concave is formed between the nodes between which the fiber cuts and a convex is formed between the gathered nodes between which the fiber shrinks, so that the colorant is thermally fused to the PTFE resin and confined in the convex portion to be stabilized.

Figure 5:
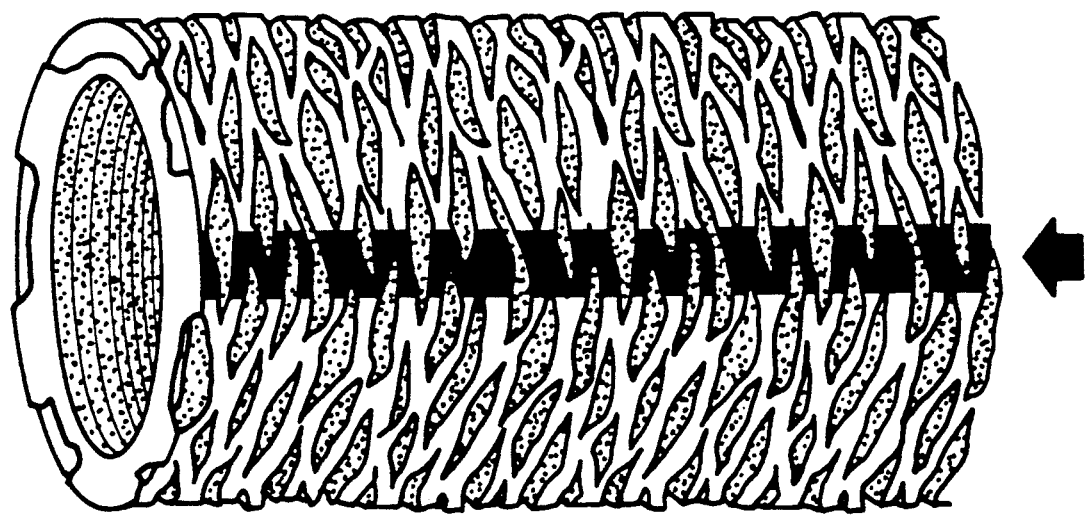
FIG. 5 is a perspective view of a porous PTFE material in which a colored line is given according to the method of the present invention.
Figure 6:
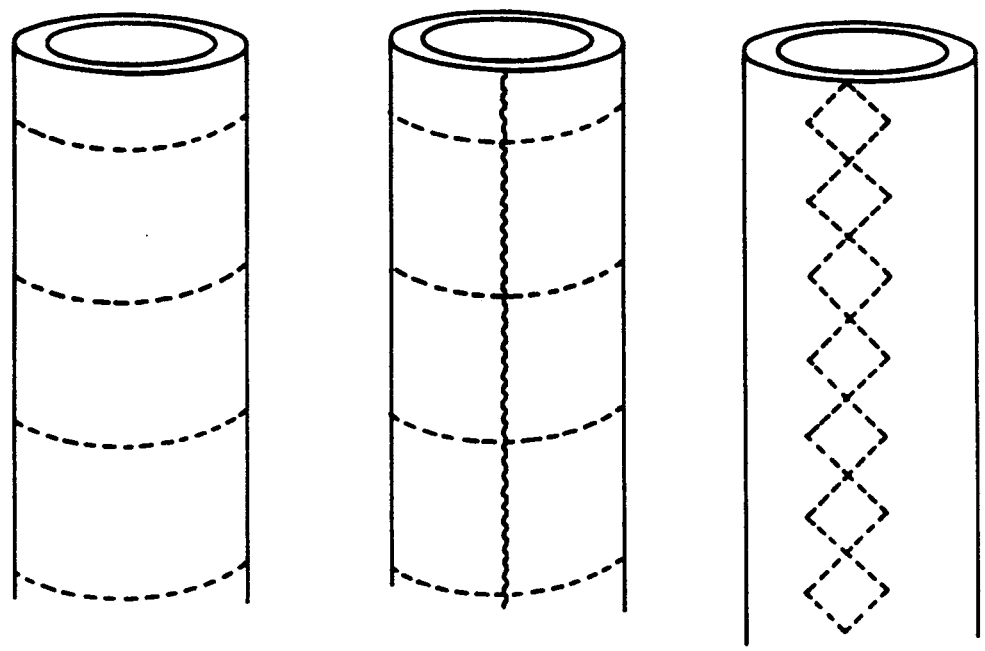
FIG. 6 is schematic views of pattern examples of various colored lines (dotted lines).
Figure 6:
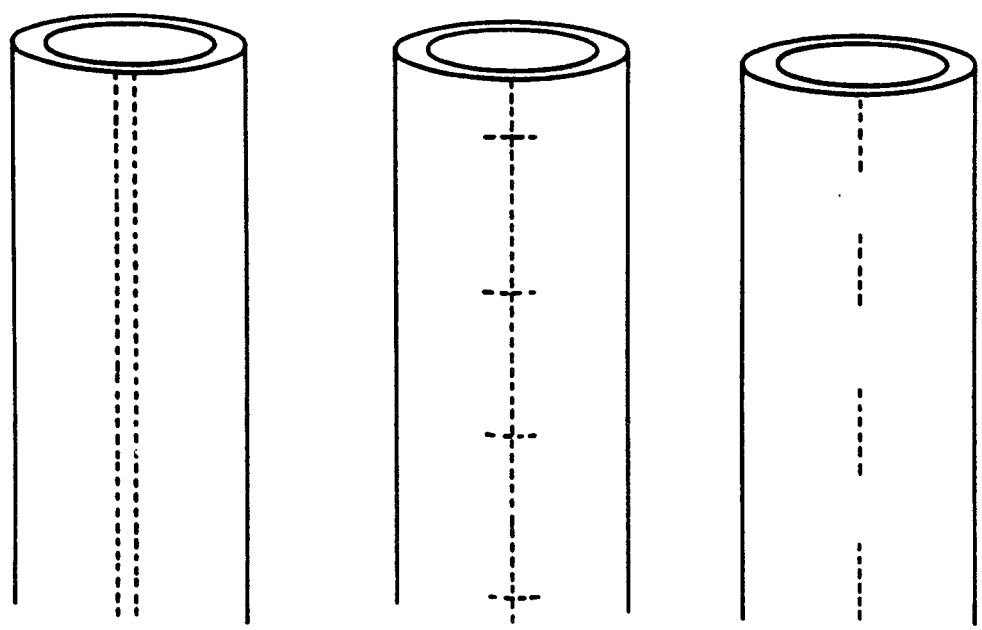

FIG. 5 is a perspective view of a colored porous PTFE tube (a finished article) having a colored line 4 provided by the method of the present invention, which has concave portions. FIG. 6 shows pattern examples of various colored lines (dotted lines).

Figure 4:
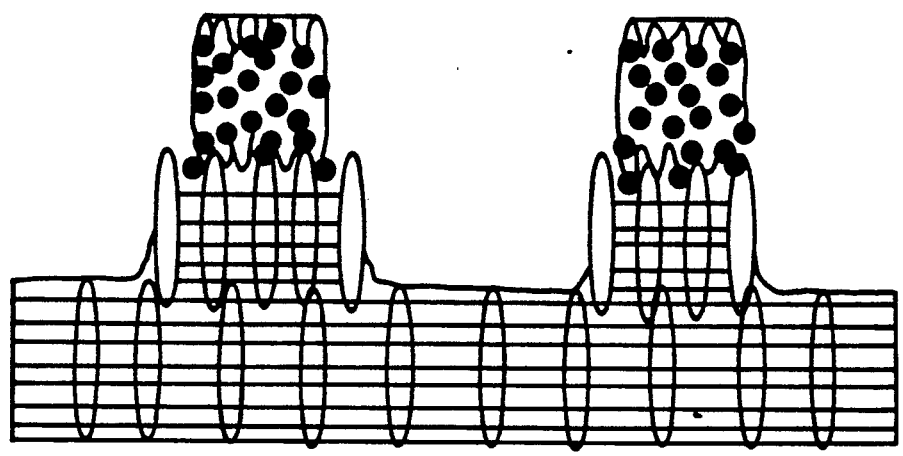
FIG. 4 is a schematic view showing that the heating causes a final shrinkage between the nodes so that the colorant is fused and confined.

As is clear from FIG. 4, since the heating shrinks the pores to confine the colorant in the PTFE resin and the colorant is thermally fused to the PTFE resin in the colored porous PTFE material according to the present invention, both of the above actions can effectively suppress the deposition of the colorant. In addition, since the distance between the nodes of the portion impregnated with the colorant is shortened, the porous structure is also maintained.

The porous PTFE material may be prepared basically according to the Japanese Patent Kokoku Publication No. 13560/1967. The porous PTFE material may have any shape selected from a tube, a sheet, a rod or the like. Among them, the method of present invention is suitable for the coloring of, particularly, a porous PTFE material tube (a tube structure).

Firstly, unsintered PTFE powder is mixed with a lubricating liquid, extruded and preformed to a desired shape by a rolling or the like. After the lubricating liquid is optionally removed from the preformed material, the preformed material is stretched at least monoaxially. Then, during fixing the stretched material so that it does not shrink, it is heated at at least 327° C. which is a melting point of the PTFE resin, preferably 350° to 380° C. so as to sinter and fix the stretched structure to prepare a porous PTFE material having the improved strength. The porous PTFE material has a fine fiber structure consisting of fibers and nodes connected to one another through the fibers. A distance of the fiber between the adjacent nodes is usually from 10 to 200 $\mu$m, preferably from 20 to 60 $\mu$m. A porosity is usually from 40 to 90%, preferably from 60 to 90%.

The colorant used according to the present invention is preferably insoluble in an aqueous or nonaqueous solvent in view of the suppression of the deposit. The colorant can not be preferably modified or degraded by the heat. Accordingly, the colorant is usually an inorganic pigment. Specific examples of the colorant are carbon black (C) and black iron oxide ($Fe_3O_4$) as a black pigment, chromium oxide ($Cr_2O_3$), titanium cobalt green ($Co_2TiO_4 \cdot nNi_2TiO_4 \cdot mZn_2TiO_4$) and cobalt chromium green ($CoCr_2O_4$) as a green pigment, and cobalt blue as a blue pigment. When the porous PTFE material is used as a medical material including a blood vessel, the blue pigment, for example, cobalt blue is preferable since blood is red. Cobalt blue includes $CoAl_2O_4$, Co(Al,Cr)$O_4$, (Co,Zn)AlO$_4$, mixtures thereof, mixtures with $TiO_4$ having a controlled color tone. A particle size of the colorant is usually from 0.01 to 5 $\mu$m, preferably from 0.1 to 1 $\mu$m.

Usually, the porous PTFE material is impregnated with the colorant by coating a liquid in which the colorant is dissolved or dispersed in an organic solvent, for example, an alcohol (e.g. methyl alcohol, ethyl alcohol and isopropyl alcohol) and acetone. Since PTFE is hydrophobic, PTFE seldom gets wet to be impregnated with an aqueous solvent. But, the organic solvent is absorbed well in PTFE and pores between nodes can contain the colorant together with this absorption. Although the porous PTFE material previously impregnated with the organic solvent may coated with the colorant, it is difficult to control a range impregnated with the colorant due to a large diffusion degree.

Theoretically, a coating property of the colorant has a relationship with a deposition property. Namely, easiness to coat means easiness to deposit. The porous PTFE material has the pores to make the coating and impregnation of the colorant easy when the colorant is coated. After the impregnation of the colorant, the deposition of the colorant is made difficult by closing the pores.

It is supposed that because the porous PTFE material is heated at at least the melting point of the porous material and the portion impregnated with the colorant between nodes is shrunk, the impregnated colorant is fused to the PTFE resin and confined in the porous PTFE material. The porous PTFE material can be heated at at least the melting point thereof according a procedure described in Japanese Patent Kokoku Publication No. 1656/1983 (corresponding to U.S. Pat. No. 4,332,035, the disclosure of which is incorporated herein by reference). A heating temperature is usually from 390° to 1,000° C., preferably from 400° to 900° C. A heating time is usually from 1 to 1,000 seconds, preferably from 60 to 600 seconds.

By heating a portion of the porous PTFE tube, for example, an external portion of the porous PTFE tube, some of the fibers connecting the nodes one another are cut and some of the nodes gather so that a rough network structure having a pore size of from several tens micrometers to several millimeters is finally formed in the heated surface to give a porous PTFE material having portions in which the orientation of the fine fiber structure is strong in one direction and portions in which that is strong in another direction perpendicular to said direction. In this rough structure, the concaves correspond to the pores between the nodes extended by the cut of the fibers, and the convexes correspond to the pores between the nodes closed by the gathering of the nodes.

The above Publication has no disclosure that the porous PTFE material supports another substance therein. It is supposed that if the substance is previously contained in the pore of the convex portion, the structure in which the substance is confined in the shrunk pore of the convex portion is obtained. Since this procedure gives sufficient heat to cut the PTFE fibers and melt the PTFE resin, the substance is thermally fused to the molten PTFE resin. According to the method of the present invention, it is difficult for the colorant to be liberated from the porous PTFE material and then deposit due to effects of both the fusion and the confinement.

In order to heat the portion impregnated with the colorant at at least the melting point of the PTFE resin, in the case that the porous PTFE material is a sheet, the surface coated and impregnated with the colorant may be contacted with a heating belt having a temperature of at least the melting point of the PTFE resin. In the case that the porous PTFE material is a tube, an external portion thereof may be coated and impregnated with the colorant, a stainless steel rod is inserted in a bore of the porous PTFE material tube and then the porous PTFE material tube is heated by blowing hot air against an external surface of the porous PTFE material tube. Since an internal surface of the tube is contacted with the stainless steel rod which is not heated, the heat escapes through the stainless steel rod so that the internal surface is at a lower temperature than the external surface. In this way, the porous PTFE material can be partially heated.

Preferred Embodiments of the Invention

The present invention is illustrated by following Examples which do not limit the present invention.

EXAMPLE 1

Polytetrafluoroethylene resin fine powder (F 104 manufactured by Daikin Industries Ltd.) (100 parts by weight) was mixed with a fluid lubricant DRYZO-LE ® (25 parts by weight) and then extruded by ram extrusion to prepare a tube. After DRYZOLE was air-dried, the tube was heated at 250° C. and stretched by 500%. Then, the tube was calcined at 380° C. for one minute to prepare a porous PTFE tube having an internal diameter of 4 mm, an external diameter of 5.5 mm, a porosity of 75% and an average distance between nodes of 30 μm.

Cobalt blue powder ($CoAlO_4$, average particle size: 0.4 μm) as a colorant was dispersed in ethyl alcohol to prepare a dispersion having a solid content of 0.2% by weight.

The dispersion was coated on an external surface of the porous PTFE tube longitudinally to form a straight line having a width of about 1 mm. Then, a stainless steel rod having a diameter of 4 mm was inserted in the tube and the tube was heated at 900° C. for 30 seconds with fixing both ends of the tube.

EXAMPLE 2

The same procedure as in Example 1 was repeated except that the cobalt blue dispersion in ethanol was coated on the external surface of the porous PTFE tube circumferentially to form ring lines in which each line has a width of 1 mm and each distance between adjacent lines is 2 cm.

EXAMPLE 3

The same procedure as in Example 1 was repeated except that the tube was heated at 400° C. for 5 minutes, after the cobalt blue dispersion in ethanol was coated on the external surface of the porous PTFE tube, the stainless steel rod having the diameter of 4 mm was inserted in the tube and both ends of the tube were fixed.

EXAMPLE 4

The same procedure as in Example 1 was repeated except that isopropyl alcohol was used as the solvent for dispersing cobalt blue.

EXAMPLE 5

The same procedure as in Example 1 was repeated except that methyl alcohol was used as the solvent for dispersing cobalt blue.

COMPARATIVE EXAMPLE 1

The same procedure as in Example 1 was repeated except that the cobalt blue dispersion in ethanol was coated after the stretch by 500% and before the calcination at at least the melting point.

COMPARATIVE EXAMPLE 2

The same procedure as in Example 1 was repeated except that the cobalt blue dispersion was coated after (not before) the heat treatment at 900° C. for 30 minutes.

COMPARATIVE EXAMPLE 3

The same procedure as in Example 1 was repeated except that only ethanol was coated instead of the cobalt blue dispersion in ethanol.

A sample having a length of 50 cm was cut from each porous PTFE tube prepared in Examples 1–5 and Comparative Examples 1–3. The sample was cut into pieces each having a length of about 1 cm and deaerated under vacuum in ethanol and pure water, and then the mixture was stirred at 37° C. for 2 hours. The sample pieces were removed, and the liquid was dried. The presence or absence of a residue was observed visually and by a FE-SEM (scanning electron microscope) and an elemental analysis of the residue was performed.

The results are shown in Table 1.

TABLE 1

| Sample | Ex. 1 | Ex. 2 | Ex. 3 | Ex. 4 | Ex. 5 | Com. Ex. 1 | Com. Ex. 2 | Com. Ex. 3 |
|---|---|---|---|---|---|---|---|---|
| Residue (Visually) | None | None | None | None | None | Almost none | Large amount | None |
| Residue (Electron microscope) | None | None | None | None | None | Slight amount | Yes | None |
| Elemental analysis of residue | — | — | — | — | — | Co, Al | Co, Al | — |

The present invention can provide a colored porous PTFE material without degrading porosity and with depressing the deposition of a colorant. According to the present invention, an artificial blood vessel can be provided with a reference line having high safety. A line for indicating a length can be provided in addition to a straight line, because this provision can be performed after a step for changing a size such as the expansion is performed on the porous PTFE material.

What is claimed is:

1. A method for preparing a colored porous polytetrafluoroethylene material which comprises the steps of:
    a) impregnating a porous polytetrafluoroethylene material with a colorant, said material having a structure comprising fibers and nodes connected to one another through the fibers; and
    b) heating at least a portion of the porous material impregnated with the colorant at a temperature of at least a melting point of the porous material to form convex regions and concave regions on the porous material, an amount of the nodes in the concave regions being greater than an amount of the nodes in the concave regions, wherein the colorant being substantially confined in the convex regions.

2. The method according to claim 1, wherein the porous material is impregnated by coating the porous material with a liquid comprising the colorant dissolved or dispersed in an organic solvent.

3. The method according to claim 1, wherein the colorant is an inorganic pigment.

4. The method according to claim 2, wherein the colorant is cobalt blue and the organic solvent is an alcohol.

5. The method according to claim 1, wherein a heating temperature is from 400° to 900° C. and a heating time is from 60 to 600 seconds.

6. The method according to claim 1, further comprising the step of heating the porous polytetrafluoroethylene material before impregnating to calcine the porous polytetrafluoroethylene material.

7. The method according to claim 6, wherein the porous polytetrafluoroethylene material is heated to at least a melting temperature of the porous polytetrafluoroethylene material to calcine the porous polytetrafluoroethylene material.

8. The method according to claim 6, wherein the porous polytetrafluoroethylene material is heated to a temperature range of 350° C. to 380° C. to calcine the porous polytetrafluoroethylene material.

9. A method for preparing a colored porous polytetrafluoroethylene material which comprises the steps of:
   a) heating a porous polytetrafluoroethylene material having a structure comprising fibers and nodes connected to one another through the fibers to calcine the porous polytetrafluoroethylene material;
   b) impregnating the porous polytetrafluoroethylene material with a colorant; and
   c) heating at least a portion of the porous material impregnated with the colorant at a temperature of at least a melting point of the porous material.

10. The method according to claim 9, wherein the porous material is impregnated by coating the porous material with a liquid comprising the colorant dissolved or dispersed in an organic solvent.

11. The method according to claim 9, wherein the colorant is an inorganic pigment.

12. The method according to claim 10, wherein the colorant is cobalt blue and the organic solvent is an alcohol.

13. The method according to claim 9, wherein heating temperature is from 400° C. to 900° C. for 60 to 600 seconds in step c.

14. The method according to claim 9, wherein the porous polytetrafluoroethylene material is heated to at least a melting temperature of the porous polytetrafluoroethylene material in step a.

15. The method according to claim 14, wherein the porous polytetrafluoroethylene material is heated to a temperature range of 350° C. to 380° C. in step a.

* * * * *